United States Patent
Newton

(10) Patent No.: US 6,957,454 B1
(45) Date of Patent: Oct. 25, 2005

(54) MATTRESS COVER WITH MASSAGING MECHANISM AND HEATING ELEMENT

(76) Inventor: Kitala Ann Newton, 4924 Unseld Blvd., Louisville, KY (US) 40218

( * ) Notice: Subject to any disclaimer, the term of this patent is extended or adjusted under 35 U.S.C. 154(b) by 0 days.

(21) Appl. No.: 10/406,045

(22) Filed: Apr. 2, 2003

Related U.S. Application Data

(60) Provisional application No. 60/369,622, filed on Apr. 2, 2002.

(51) Int. Cl.$^7$ ............................ A61H 1/00; A61F 7/00
(52) U.S. Cl. .................... 5/421; 5/691; 5/933; 601/49
(58) Field of Search ........................... 5/109, 421, 915, 5/933, 934, 935, 936, 937, 943, 691, 983; 601/49, 51, 98, 86, 90, 108, 111, 112

(56) References Cited

U.S. PATENT DOCUMENTS

| | | | | |
|---|---|---|---|---|
| 2,425,655 A | * | 8/1947 | Tompkins | 601/57 |
| 2,773,498 A | * | 12/1956 | Himmelman | 601/98 |
| 2,910,977 A | * | 11/1959 | Jeter | 601/57 |
| 4,388,738 A | * | 6/1983 | Wagner | 5/421 |
| 4,423,308 A | * | 12/1983 | Callaway et al. | 219/217 |
| 4,494,260 A | * | 1/1985 | Olds et al. | 5/613 |
| 4,625,487 A | * | 12/1986 | Blakeway | 5/613 |
| 4,955,095 A | * | 9/1990 | Gerrick | 5/691 |
| 5,787,525 A | * | 8/1998 | Sugihara et al. | 5/421 |

* cited by examiner

*Primary Examiner*—Michael F. Trettel
(74) *Attorney, Agent, or Firm*—Roy, Kiesel, Keegan and DeNicola

(57) ABSTRACT

A mattress cover with massaging mechanism and heating element built in that includes a foam padding structure, positionable over the top of a mattress and having a cavity provided therein, a padding structure cover and a number of multi-fold, massaging ridge members that pass through the cavity and into connection with a drive mechanism. The drive mechanism being controlled by a remote control unit provided to allow a user to adjust the frequency and intensity of the massage, providing movement of the multi-fold, massaging ridge members generated by operation of the drive mechanism while laying down on the padding structure cover; a heating element is optionally added to the padding structure to cover across the user to receive heat treatment while receiving a massage.

1 Claim, 1 Drawing Sheet

US 6,957,454 B1

MATTRESS COVER WITH MASSAGING MECHANISM AND HEATING ELEMENT

This application claims the benefit of Provisional application Ser. No. 60/369,622, filed Apr. 2, 2002.

TECHNICAL FIELD

The present invention relates to massaging mechanisms the like and more particularly to a massaging mattress cover system that includes a cover assembly including bottom pad structure and a top pad structure cover member; a massage mechanism including an electrically powered drive mechanism having multiple rotary drive outputs each connected to a ridged, rotary massaging element in a manner such that each rotary drive output directly rotates the ridged, rotary massaging element connected thereto when the electrically powered drive mechanism is in operation; an electrical heating element; and a control unit in controlling connection with the electrically powered drive mechanism and the electrical heating element and including a remote user control that allows the user to control the rotational speed of the rotational drive outputs of the electrically powered drive mechanism and the temperature of the electrical heating element; the bottom pad structure having an open top, four sidewalls and a bottom portion that define an open-topped massaging element receiving cavity having therein the multiple, ridged, rotary massaging elements such that each rotary massaging element has a first massage element end rotatably positioned through a first sidewall and into connection with its respective rotary drive output; the electrical heating element being positioned within the top pad structure cover member near enough to a user contact surface to transfer heat effectively to the user; the top pad structure cover member being securable to the bottom pad structure in a manner to cover the top opening of the open-topped massaging element receiving cavity while being supported by the multiple ridged, rotary massaging elements; the top pad structure cover member being sufficiently thin such that the height of any given point on the outer user contact surface of the top pad structure cover member varies directly with the various positions of the multiple ridged, rotary massaging elements allowing a user laying on the outer user contact surface of the top pad structure cover member to receive a massage while not being directly contacted by the multiple, rotating, ridged, rotary massaging elements.

BACKGROUND ART

Many individuals enjoy receiving a massage. This is particularly true just before bedtime. It would be a benefit for these individuals to have a massaging mattress cover system which could be placed over a mattress, and which could be slept on after the massage was over. Such a system would allow an individual to enjoy a massage prior to falling asleep. Because massage therapy is often more effective when the muscles are heated, it would be a further benefit if the outer cover of a massaging mattress cover were fitted with a heating element.

GENERAL SUMMARY DISCUSSION OF INVENTION

It is thus an object of the invention to provide a mattress cover with massaging mechanism and heating element that includes a cover assembly including bottom pad structure and a top pad structure cover member; a massage mechanism including an electrically powered drive mechanism having multiple rotary drive outputs each connected to a ridged, rotary massaging element in a manner such that each rotary drive output directly rotates the ridged, rotary massaging element connected thereto when the electrically powered drive mechanism is in operation; an electrical heating element; and a control unit in controlling connection with the electrically powered drive mechanism and the electrical heating element and including a remote user control that allows the user to control the rotational speed of the rotational drive outputs of the electrically powered drive mechanism and the temperature of the electrical heating element; the bottom-pad structure having an open top, four sidewalls and a bottom portion that define an open-topped massaging element receiving cavity having therein the multiple, ridged, rotary massaging elements such that each rotary massaging element has a first massage element end rotatably positioned through a first sidewall and into connection with its respective rotary drive output; the electrical heating element being positioned within the top pad structure cover member near enough to a user contact surface to transfer heat effectively to the user; the top pad structure cover member being securable to the bottom pad structure in a manner to cover the top opening of the open-topped massaging element receiving cavity while being supported by the multiple ridged, rotary massaging elements; the top pad structure cover member being sufficiently thin such that the height of any given point of the outer user contact surface of the top pad structure cover member varies directly with the positions of the multiple ridged, rotary massaging elements allowing a user laying on the outer user contact surface of the top pad structure cover member to receive a massage while not being directly contacted by the multiple, rotating, ridged, rotary massaging elements.

Accordingly, a mattress cover with massaging mechanism and heating element is provided. The mattress cover with massaging mechanism and heating element includes a cover assembly including bottom pad structure and a top pad structure cover member; a massage mechanism including an electrically powered drive mechanism having multiple rotary drive outputs each connected to a ridged, rotary massaging element in a manner such that each rotary drive output directly rotates the ridged, rotary massaging element connected thereto when the electrically powered drive mechanism is in operation; an electrical heating element; and a control unit in controlling connection with the electrically powered drive mechanism and the electrical heating element and including a remote user control that allows the user to control the rotational speed of the rotational drive outputs of the electrically powered drive mechanism and the temperature of the electrical heating element; the bottom pad structure having an open top, four sidewalls and a bottom portion that define an open-topped massaging element receiving cavity having therein the multiple, ridged, rotary massaging elements such that each rotary massaging element has a first massage element end rotatably positioned through a first sidewall and into connection with its respective rotary drive output; the electrical heating element being positioned within the top pad structure cover member near enough to a user contact surface to transfer heat effectively to the user; the top pad structure cover member being securable to the bottom pad structure in a manner to cover the top opening of the open-topped massaging element receiving cavity while being supported by the multiple ridged, rotary massaging elements; the top pad structure cover member being sufficiently thin such that the height of any given point of the outer user contact surface of the top pad structure cover member varies directly with the positions of the multiple ridged, rotary massaging elements allowing a user laying on the outer user contact surface of the top pad structure cover member to receive a massage while not being directly contacted by the multiple, rotating, ridged, rotary massaging elements.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein.

EXEMPLARY MODE FOR CARRYING OUT THE INVENTION

Figure 1:
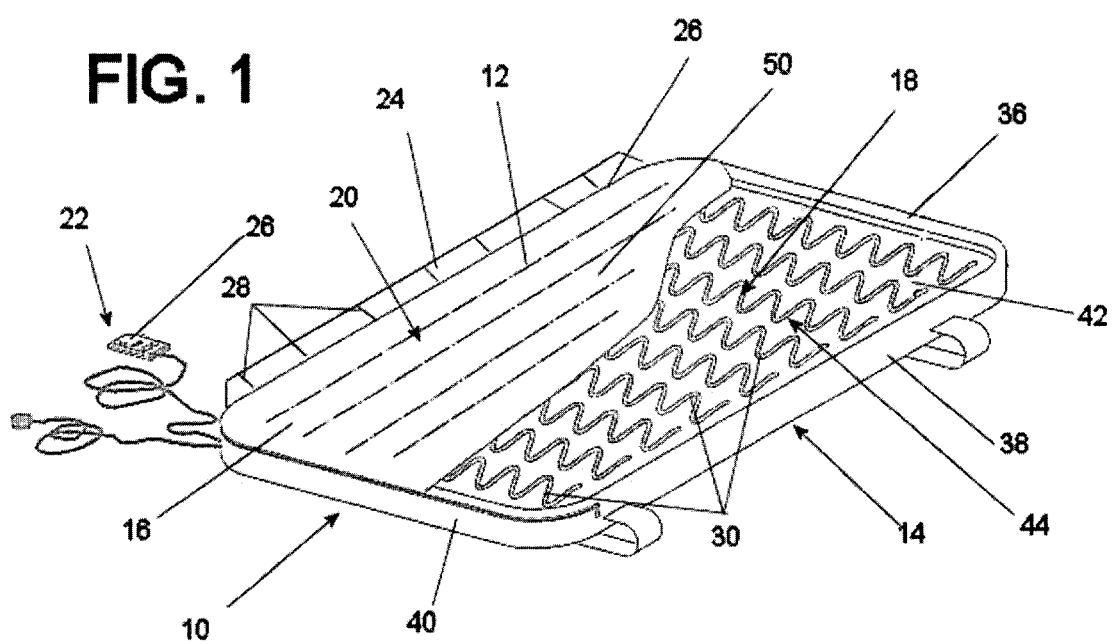
FIG. 1 is a perspective view of an exemplary embodiment of the mattress cover with massaging mechanism and heating element of the present invention.

FIG. 1 shows various aspects of an exemplary embodiment of the mattress cover with massaging mechanism and heating element of the present invention generally designated 10. Mattress cover with massaging mechanism and heating element built in 10 includes a cover assembly, generally designated 12, including bottom pad structure, generally designated 14 and a top pad structure cover member, generally designated 16; a massage mechanism, generally designated 18; a heating element, generally designated 20; and a control unit, generally designated 22.

Massage mechanism 18 includes an electrically powered drive mechanism, generally designated 24, attached to the outer surface of a sidewall 26 of bottom pad structure 14 and having multiple rotary drive outputs 28 each connected to a ridged, rotary massaging element, generally designated 30, in a manner such that each rotary drive output 28 directly rotates the ridged, rotary massaging element 30 connected thereto when the electrically powered drive mechanism 24 is in operation.

Control unit 22 is in controlling connection with the electrically powered drive mechanism 24 and the electrical heating element 20 and includes a remote user control 26 that allows the user to control the rotational speed of the rotational drive outputs 28 of electrically powered drive mechanism 24 and the temperature of the electrical heating element 20.

Bottom pad structure 14 has an open top, four sidewalls 26, 36,38,40 and a bottom portion 42 that define an open-topped massaging element receiving cavity 44 having therein the multiple, ridged, rotary massaging elements 30 such that each rotary massaging element has a first massage element end rotatably positioned through sidewall 26 and into connection with its respective rotary drive output 28. Electrical heating element 20 is positioned within top pad structure cover member 16 near enough to a user contact surface 50 to transfer heat effectively to the user. Top pad structure cover member 16 is securable to bottom pad structure 14 in a manner to cover the top opening of the open-topped massaging element receiving cavity 44 while being supported by the multiple ridged, rotary massaging elements 30. Top pad structure cover member 16 is sufficiently thin such that the height of any given point on the outer user contact surface 50 varies directly with the various positions of the ridged, rotary massaging element 30 directly beneath that point allowing a user laying on the outer user contact surface 50 to receive a massage while not being directly contacted by the multiple, rotating, ridged, rotary massaging elements 30. The faster the massaging elements 30 rotate, the more vigorous the massaging action.

It can be seen from the preceding description that mattress cover with massaging mechanism and heating element built in has been provided.

It is noted that the embodiment of the mattress cover with massaging mechanism and heating element built in described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A massaging mattress cover system comprising:

a cover assembly including a bottom pad structure and a top pad structure cover member;

a massage mechanism including an electrically powered drive mechanism having multiple rotary drive outputs each connected to a ridged, rotary massaging element in a manner such that each rotary drive output directly rotates the ridged, rotary massaging element connected thereto when the electrically powered drive mechanism is in operation;

an electrical heating element; and a control unit in controlling connection with the electrically powered drive mechanism and the electrical heating element and including a remote user control that allows the user to control the rotational speed of the rotational drive outputs of the electrically powered drive mechanism and the temperature of the electrical heating element;

the bottom pad structure having an open top, four sidewalls and a bottom portion that define an open-topped massaging element receiving cavity having therein the multiple, ridged, rotary massaging elements such that each rotary massaging element has a first massage element end rotatably positioned through a first sidewall and into connection with its respective rotary drive output;

the electrical heating element being positioned within the top pad structure cover member near enough to a user contact surface to transfer heat effectively to the user; the top pad structure cover member being securable to the bottom pad structure in a manner to cover the top opening of the open-topped massaging element receiving cavity while being supported by the multiple ridged, rotary massaging elements; the top pad structure cover member being sufficiently thin such that the height of any given point on the outer user contact surface of the top pad structure cover member varies directly with the various positions of the multiple ridged, rotary massaging elements allowing a user laying on the outer user contact surface of the top pad structure cover member to receive a massage while not being directly contacted by the multiple, rotating, ridged, rotary massaging elements.

\* \* \* \* \*